United States Patent [19]

Turner

[11] Patent Number: Plant 6,486

[45] Date of Patent: Dec. 27, 1988

[54] ANIGOZANTHOS PLANT NAMED BUSH EMERALD

[75] Inventor: Mervyn L. Turner, Monbulk, Australia

[73] Assignee: Biotech Plants Pty. Ltd., Somersby, Australia

[21] Appl. No.: 33,813

[22] Filed: Apr. 3, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Kangaroo Paw plant (genus Anigozanthos) named Bush Emerald having a red and green inflorescence, narrow foliage developing a glaucous surface texture, spring flowering in outdoor temperate climate, and superior resistance to Alternaria species.

1 Drawing Sheet

The present invention relates to a new and distinctive cultivar of Anigozanthos (Kangaroo Paw), named Bush Emerald. Kangaroo Paw is the popular name applied to all species of the botanical genera Anigozanthos Labill and Macropidia Harv and their variants and hybrids.

Anigozanthos Labill is a genus of eleven described species of herbaceous perennial plants of the family Haemodoraceae, and which are endemic to the south-western region of western Australia. These species, together with the closely allied monotype *Macropidia fuliginosa* (Hook.) Druce, are as above noted jointly referred to by the popular common name Kangaroo Paws.

Wild populations of Kangaroo Paws grow in a warm temperature Mediterranean climate (Summer drought). Vitality is at a minimum in late Summer/early Autumn, and some species show or tend to a full deciduous dormancy at this time. Active vegetative growth is reinstated with the onset of lower temperatures and rainfall in the Autumn (Fall). The flowering season varies considerably between species, but the display period is normally of several months somewhere within the range of late Winter to mid-Summer.

Mature plants consist of a clump of leaf fans arising from ramified rhizome which exists at immediate subsurface soil levels. Rhizome extends and branches by annual growth and is more or less persistent. Leaves and roots are replenished on an annual basis.

Leaves arise from rhizome buds and exist as fans of alternate ensheathing leaves arranged on an equitant conduplicate pattern, and with very short internodes.

Individual leaves are normally relatively straight and narrow in length, being approximately parallel sided in the lower half or more, and tapering to an acute point above. As new leaves arise in the center of each fan between the next youngest leaves, older leaves are progressively displaced at an angle. In some species older leaves may become distinctly recurved.

There is variation between species in the stature of leaf fans and in the relative width of individual leaves. In the largest species, leaves may be one meter in length and up to five centimeters wide. In the smallest species, leaves may be ten centimeters in length and one centimeter wide.

The active apical meristem in a leaf fan is located near the base of the fan during the active vegetative growth stage. Eventually, a rapid increase in length of successive internodes occurs accompanied by a decrease in leaf size and followed by a differentiation of the apex, the overall process forming a flower stem. The overall length of the flower stem varies between 1.5 and 2.5 times the length of the basal leaves of the leaf fan according to the species.

The inflorescence per se is a unilateral raceme, both series of sub-sessile to shortly pedunculate alternating flowers being oriented in the same direction. Each peduncle is marked by a pointed bract shorter than the flower. The flower is itself bilaterally symmetrical consisting of a spherical tri-locular basal ovary extending into an initially narrower and cylindrical perianth which broadens and flattens and terminates in six lobes. At anthesis the lobes which are contiguous in bud, separate and reflex, the degree varying with species. The style is simple, free, and about as long as the perianth, and terminates in a small sub spherical stigma. The six anthers have short to very short filaments, the points of insertion being towards the apex of the perianth.

Three more or less distinctive patterns in the architecture of the flower stem can be recognized. In some species the architecture is simple, with the stem being simple and terminating in a solitary raceme. In other species, the stem is initially simple but forks immediately sub-terminally, each fork terminating in a raceme. In some species, the stem is initially simple but then branches more or less dichotomously, the node being subtended by a shortened leaf. Secondary branching may occur, but eventually most branches fork, each ultimate branch or fork terminating in a raceme.

In one extreme in some species, the length of the overall flower stem can exceed two meters. At the other extreme, in some species, the stem may rarely be longer than twenty centimeters.

Racemes may be few to many flowered and individual flowers from three centimeters to ten centimeters in length varying with species.

In all species the flowers, and in all but one species the stem, are clothed with a close indumentum of velvet texture. The indumentum is colored and the stem, ovary, and perianth may be distinctively colored. Flower color or pattern of coloration normally applies to that of this indumentum. Development of pigmentation is to some degree a function of environmental conditions, especially of temperature and total irradiance during bud development.

The new cultivar Bush Emerald was created by the inventor as a result of a controlled crossing of a selected genotype of the species *Anigozanthos viridis* Endl. (seed parent) with a selected genotype of the species *Anigozanthos manglesii* D. Don (pollen parent).

Asexual reproduction by applicant in Monbulk, Victoria, Australia by division of the rhizome and by aseptic multiplication of leaf shoots including apical meristem on nutrient media has reproduced the unique features of the new cultivar through successive generations.

The following characteristics distinguish the new cultivar from both its parents and from other Kangaroo Paws known and used in the ornamental horticultural industry.

1. The cultivar exhibits superior resistance compared with either parent to Alternaria species, these air-born fungal species which are the major hazard to Kangaroo Paws in cultivation. Both parents were themselves selected as genotypes having relatively superior resistance when compared with other cultivars in the species.

2. The characteristics of the foliage most closely resemble those of the seed parent, and the characteristics of the inflorescence most closely resemble those of the pollen parent.

3. The combination of flower and foliate characteristics is generally more decorative and pleasing than in either parent, and the overall color contrasts are distinctive and interesting.

4. The leaves are a blue-green and develop a waxy, glaucous bloom; the leaves are narrow, upright, and sub-parallel in each leaf fan, and rarely longer than 40 cm.

5. The overall inflorescence is usually simple, with a terminal raceme of 12 to 18 flowers and between 60 cm and 90 cm in length; occasional single forked stems arise, each fork having a terminal raceme; mature flowers are approximately 10 cm in length.

6. The upper part of the flower stem, the axis of the raceme, and the ovary of the flowers are clothed in a red indumentum; the indumentum of the perianth of the flower is deep green. Buds are paler in color, with pigmentation increasing as the buds develop.

7. Growth is vigorous and young plants quickly establish clumps of leaf fans by rhizome growth, and such growth is superior to either parent. Maximum growth rates of young plants are exhibited where maximum day temperatures are in the range 18 degrees Celsius to 23 degrees Celsius and minimum night temperatures are in the range of 10 to 15 degrees Celsius.

The accompanying colored photographs illustrate the new cultivar, with the colors being as true as it is reasonably possible to obtain in colored reproductions of this type. The photograph at the top is a perspective view of a plant of Bush Emerald and the photograph at the bottom is an enlarged showing of the flower.

The following is a detailed description of Bush Emerald based on plants produced at Bush Gems Garden Nursery in Monbulk, Victoria, Australia. Color references are made to the Royal Horticultural Society Colour Chart except where general color terms of ordinary dictionary significance are used. Terms used have the same meaning and significance as those used and defined above regarding the characteristics of propagation, plant form, habit of growth, foliage, flowers and rhizome common and general to all plants of Anigozanthos.

Parentage: A hybrid of two selected genotypes of the species *Anigozanthos viridis* Endl. (seed parent) and *Anigozanthos manglesii* D. Don (pollen parent).

Propagation: Asexual by: (A) Rhizome divisions; optimum period late Summer to early Fall. (B) "In vitro" proliferation of multiple shoots from plants of apical meristem with immediate leaf primordia, with a fivefold multiplication occurring each four to five weeks on appropriate media. Rooting in four to six weeks "in vivo" at approximately 20 degrees Celsius root zone temperature in high relative humidity environment. Use of anti-transpirant sprays beneficial.

Plant description:

(A) *Form.*—Clumping, rhizomic, perennial plant suited to cultivation in containers, in gardens (in essentially frost free environments), and as a row-crop cut flower. Clumps are relatively dense.

(B) *Habit of growth.*—The main period of active growth — rhizome extension, production of new leaf fans, and induction/evocation of flowers — is Winter and Spring. Vegetative growth will continue in Summer with irrigation but flowering is rare.

(C) *Foliage.*—The basal leaves of each leaf fan are of alternate, conduplicate, ensheathing arrangement. (1) Size and shape: Basal leaves up to 35 cm long by 8 to 10 mm wide at base, more or less uniformly tapering to a point. (2) Texture: Smooth, glabrous, with a glaucous "bloom", scattered hairs along the leaf edges. (3)Color: Mature, healthy foliage varying between Green 137A and 137B. The widely spaced leaves of the flower stem decrease from approximately 25 cm in length nearer the base to a few cm near the raceme, with a corresponding increase from near glabrous to a scattered indumentum. Color is similar to color of basal leaves.

Flowers:

(A) *Flowering habit.*—Flowers in dense, unilateral biseriate racemes, normally a solitary raceme terminal to an unbranched stem. Stems very occasionally forked. Overall length of the inflorescence varies with environmental conditions but is typically in the range 60 cm to 80 cm, and rarely exceeds one meter.

(B) *Natural flowering season.*—Late Winter and Spring. Young plants produced from tissue culture may have an atypical first flowering season.

(C) *Flower bud.*—Tubular, but the perianth is constricted above the ovary, approximately 6 cm long and varying from 6 to 9 mm in diameter. The perianth lobes are fused in an enlarged, asymmetrical tip.

(D) *Flowering raceme.*—Axis somewhat convex relative to display position of flowers; the pedicels of the flowers are short, approximately 7 mm, and spaced at 15 mm intervals, each pedicel subtended by a small bract, approximately 4 mm wide and 25 mm long. The lowest flowers of the raceme open first, the perianth lobes reflexing fully through 180 degrees, buds at the anterior end progressively grown and open. A single raceme typically produces 12 to 15 flowers.

(E) *Individual flower.*—Sub-spherical basal ovary approximately 10 mm in diameter, extending into a tubular perianth 5 cm in length. The ultimate 15 mm of the perianth consists of six lobes which reflex fully on opening, eventually reclosing.

(F) *Color.*—The base of the flower stem is near glabrous, color red-purple 59A; the indumentum increases until dense in the region of the raceme where the color is red-purple 59B. The indumentum of the pedicel is marked by a narrow band of near black hairs. In the lower region the indumentum of the perianth is yellow-green 162C and progressively grades to yellow-green 152A at the tip.

Disease resistance: Resistance to fungal leaf diseases (viz. Alternaria spp.) is superior when compared to typical wild seedling Kangaroo Paws, as confirmed by field trials at various sites and seasons.

I claim:

1. A new and distinct cultivar of Anigozanthos plant named Bush Emerald, as described and illustrated, and parts thereof.

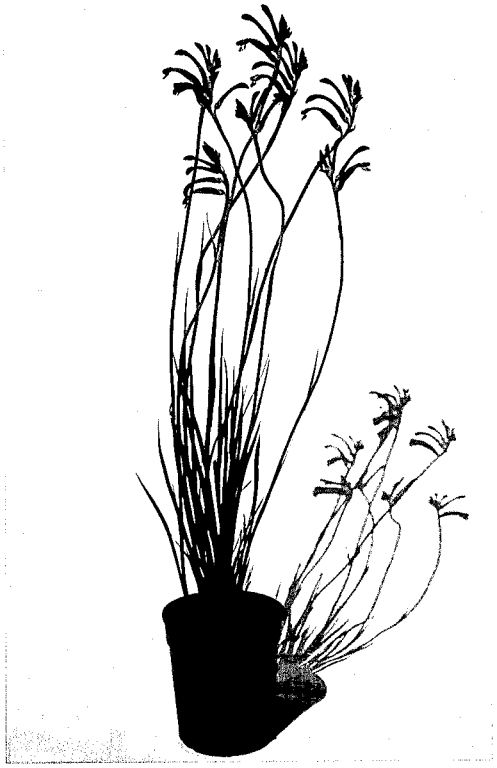
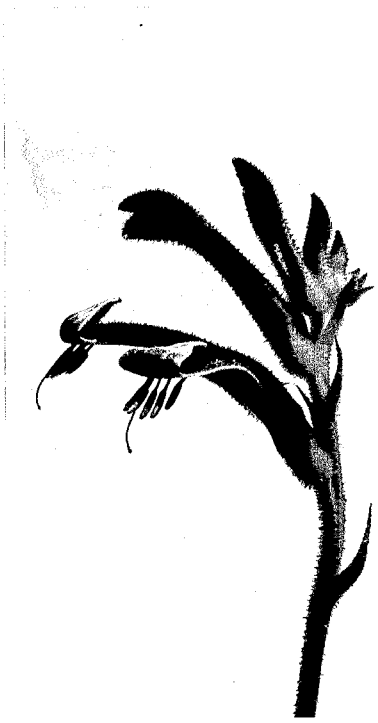

* * * * *